United States Patent [19]

Knowles

[11] Patent Number: 4,457,314
[45] Date of Patent: Jul. 3, 1984

[54] FEMALE URINE COLLECTION DEVICE AND METHOD

[75] Inventor: Adrienne Knowles, Middlebury, Conn.

[73] Assignee: Comfy Catch-A-Spec Company, Middlebury, Conn.

[21] Appl. No.: 404,143

[22] Filed: Aug. 2, 1982

[51] Int. Cl.³ .................. A61B 5/00; A61F 5/44; A61M 1/00
[52] U.S. Cl. ...................... 128/760; 128/767; 604/327; 604/329
[58] Field of Search ............... 128/760, 761; 4/144.1–144.4; 604/317, 368, 329, 331, 346, 347, 349–353, 327; 128/760, 761; 73/864.91

[56] References Cited

U.S. PATENT DOCUMENTS

| | | | |
|---|---|---|---|
| 3,613,123 | 10/1971 | Langstrom | 4/144.3 |
| 3,651,810 | 3/1972 | Ormerod | 604/329 |
| 3,918,433 | 11/1975 | Fuisz | 128/760 |
| 4,194,508 | 3/1980 | Anderson | 604/329 |
| 4,197,849 | 4/1980 | Bostick | 604/352 |

FOREIGN PATENT DOCUMENTS 491243 2/1930 Fed. Rep. of Germany ...... 604/327

OTHER PUBLICATIONS

Research Disclosure, Ormerod, Lancashire, England, Aug. 1973.

Primary Examiner—John D. Yasko
Assistant Examiner—J. L. Kruter
Attorney, Agent, or Firm—Bachman and LaPointe

[57] ABSTRACT

A urine collection device and method for females comprising a cup-shaped receiving chamber provided with a flexible lip on the periphery thereof for sealing around the urethral orifice and a duct section leading to a section of flexible tubing. The flexible tubing which leads to a compressible collection reservoir. A two way anti-back flow mechanism is provided to prevent inadvertent flow of the collected urine out of the reservoir but which upon intentional compression by a user a specimen may be obtained by forcing fluid back through the anti-back flow valve. The receiving chamber and collection reservoir are mounted in a housing of soft absorbent material which is provided with an adhesive strip for securing the collection device to the undergarment of a female.

8 Claims, 5 Drawing Figures

U.S. Patent  Jul. 3, 1984  4,457,314
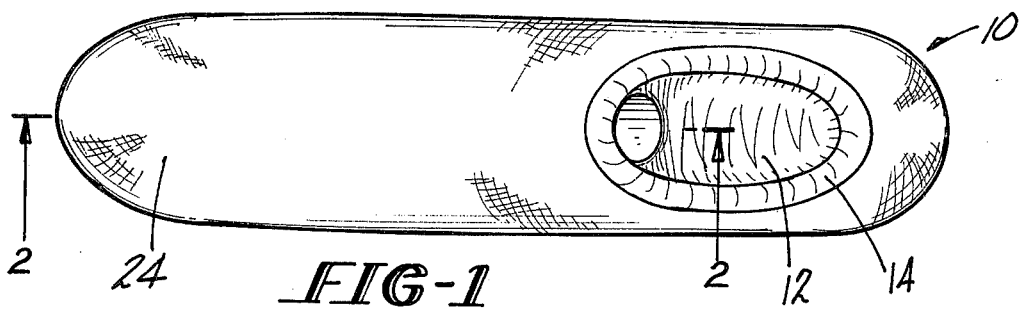
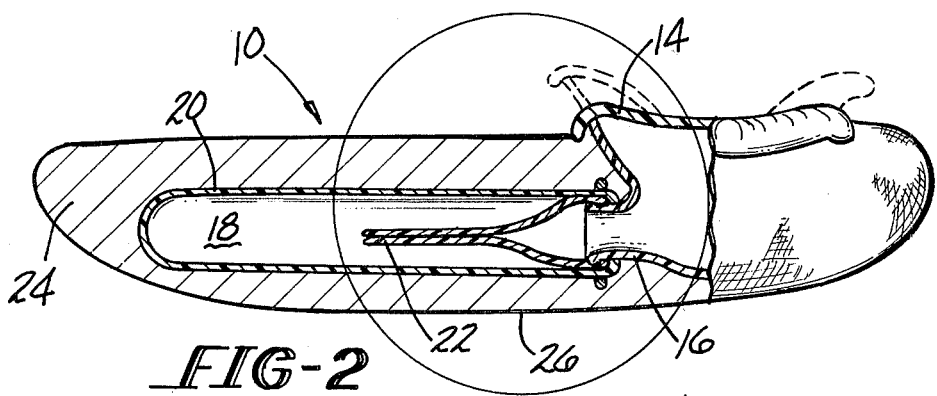
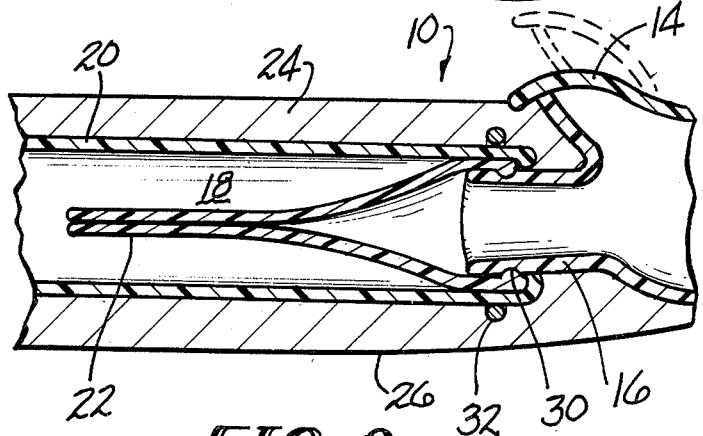
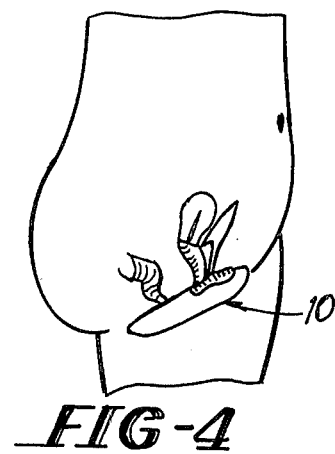
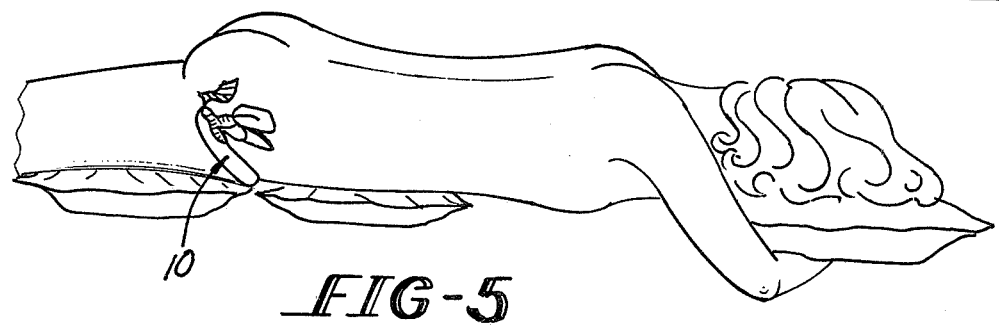

FEMALE URINE COLLECTION DEVICE AND METHOD

BACKGROUND OF THE INVENTION

The present invention relates to a urine collection device and more particularly a urine collection device for females.

Under certain circumstances it is extremely difficult to collect involuntary urine discharges or, as the case may be, urine specimens from females. For example, in the case of incontinent females such as geriatric patients or others suffering from lack of control of the sphincter muscle involuntary urine discharge collection is a problem. Likewise, in the case of continent females suffering from a number of behavioral disorders collection of periodic urine specimens is often difficult due to the patients unwillingness to cooperate.

Known urine collection devices such as bedpans or other collection vessels have proven unsatisfactory in the situations noted above for a number of reasons, the primary reason being that use of such collection vessels requires the conscious active participation of the patient. To overcome the foregoing disadvantage associated with bedpans and the like it has become common place in the prior art to form cup-like members which are to be worn over the urethral opening such as that shown in U.S. Pat. No. 4,202,058. While the foregoing overcomes the disadvantage noted above with regard to bedpans, the cup-like arrangement is not suitable for ambulatory females due to leakage problems and the fact that they are uncomfortable and interfere with the patient's freedom of motion and ability to assume various positions.

Other known prior art devices to be worn by females include absorbent garments such as that disclosed in U.S. Pat. No. 3,613,123. While these devices are generally less bulky than the cup-like devices and therefore do not interfere with freedom of motion, a number of serious problems are associated with their use. The urine held in the garment provides a haven for bacteria growth. In addition, the garments have limited capacities which results in contact between the moist garment and the patient's body thereby resulting in skin irritation and the like. Finally, the garment cannot be used to actually collect urine specimens for laboratory examination.

Naturally it is highly desirable to provide a urine collection device for females which is comfortable to wear, sanitary in use and suitable fo urine specimens. The device should be a throwaway item which is simple in construction and economic to manufacture.

Accordingly, it is a principal object of the present invention to provide a female urine collection device which may be worn comfortably by the patient.

It is a particular object of the present invention to provide a female urine collection device worn by the patient which is suitable for taking urine specimens.

It is a further object of the present invention to provide a female urine collection device suitable for specimen taking which prohibits inadvertent back flow from the device.

It is a still further object of the present invention to provide a female urine collection device which is simple in construction and economic to manufacture.

Further objects and advantages of the present invention will appear hereinbelow.

SUMMARY OF THE INVENTION

In accordance with the present invention the foregoing objects and advantages are readily obtained.

The present invention comprises a urine collection device for females and more particularly a urine collection device for incontinent females. In accordance with the present invention a collection or reservoir element in the form of a flexible membrane is provided in a housing of soft absorbent material. A moldable soft plastic receptacle is situated within the absorbent material and is provided on one end thereof with a flexible lip adapted to sealingly mate around the urethral orifice. The other end of the receptacle is provided with a tubular passage leading to the flexible membrane.

In accordance with the present invention, involuntary urine discharges are collected by the plastic receptacle and the urine flows into the flexible membrane defining a reservoir. The tubular passage acts as an anti-back flow mechanism so as to prevent inadvertent flow out of the reservoir while allowing for reverse flow when desired.

BRIEF DESCRIPTION OF THE DRAWINGS

FIG. 1 is a top view of a urinary collection device in accordance with the present invention.

FIG. 2 is a partial sectional view of the urinary collection device of FIG. 1 taken along line 2—2.

FIG. 3 is an enlarged detailed sectional view of the collection device shown in FIG. 2.

FIG. 4 is a side view showing ambulatory female with the collection device in place.

FIG. 5 is a side view showing a bedridden female with the collection device in place.

DETAILED DESCRIPTION

Referring to the drawings, the urinary collection device 10 of the present invention comprises a cup-shaped receiving chamber 12 having a flexible lip portion 14 provided on the upper peripheral surface thereof for sealing the device 10 around the urethral orifice of a female. In the preferred embodiment of the present invention, the cup-shaped receiving chamber 12 is provided with a duct section 16 in the bottom thereof for communicating urine from the cup-shaped receiving chamber 12 to a reservoir 18 defined by a flexible membrane 20. With particular reference to FIGS. 2 and 3, the duct section 16 has secured thereto by any suitable means such as spring clips, adhesives or the like, a section of flexible tubing 22 for feeding the urine from cup-shaped receiving chamber 12 to the reservoir 18 defined by the flexible membrane 20. The flexible membrane 20 likewise is secured to the duct section 16 about flexible tubing 22 in the same manner as previously described with regard to flexible tubing 22. With reference to FIGS. 2 and 3 a mechanism is shown for securing flexible membrane 20 and flexible tubing 22 to duct section 16. Duct section 16 is provided with a channel 30 and a spring clip or elastic O-ring 32 secures tubing 22 and membrane 20 in the channel 30. In accordance with the preferred embodiment of the present invention the cup-shaped receiving chamber 12, flexible membrane 20 and flexible tubing 22 are all held in a housing 24 in the form of a soft absorbent material such as gauze or the like. The cup-shaped receiving chamber 12 should be made of a moldable plastic material such as polyethylene, polypropylene or polyvinyl plastic materials. The housing 24 is provided on the bottom thereof with an adhesive strip 26 for securing the urine collection device 10 to an undergarment of a female.

With reference to FIGS. 4 and 5, the application of the collection device and the positioning thereof to a female in the urogenital region is illustrated. With the collection device 10 located in the position shown in FIGS. 3 and 4 any involuntary urine discharge is received in cup-shaped receiving chamber 12 and is led therefrom through duct section 16 and flexible tubing 22 into the reservoir 18 defined by the flexible membrane 20. Passage of urine through the flexible tubing 22 results in a capillary attraction of the walls of the flexible tubing 22 thereby sealing same so as to provide an anti-back flow mechanism prohibiting the flow of urine from the reservoir 18 back to the cup-shaped receiving chamber 12. In the event the urine collected in reservoir 18 is desired for specimen purposes one need only to squeeze the flexible membrane 20 which results in the flexible tubing being forced through the duct section 16 into the cup-shaped receiving section 12 thereby allowing passage of the urine from the reservoir 18 out through the flexible tubing 22 into a receptacle.

By way of the present invention involuntary urine discharges are readily collected in an efficient and sanitary manner without interfering with the persons normal freedom of motion and ability to assume various positions. In addition, the device of the present invention allows for the collection of urine in such a manner that the collected urine is suitable for laboratory examination.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A urine collection device for use by females which is suitable for collecting urine specimens suitable for laboratory examination comprising:
   a compressible housing;
   a receiving chamber positioned within said housing, said receiving chamber including an inlet and an outlet, said inlet having means for sealing around the urethral orifice of a female;
   a compressible reservoir provided within said housing downstream of said receiving chamber outlet; and
   two-way valve means downstream of said receiving chamber outlet and upstream of said reservoir for passing urine from said receiving chamber to said reservoir while selectively prohibiting back flow of urine from said reservoir such that upon compression of said housing and correspondingly said reservoir said two-way valve means passes back through said receiving chamber outlet thereby allowing urine in said reservoir to be passed back through said two-way valve means so as to obtain a urine specimen for laboratory examination.

2. A urine collection device according to claim 1 wherein said receiving chamber is cup-shaped and is provided thereof with a flexible lip portion defining said inlet for sealing around the urethral orifice of a female.

3. A urine collection device according to claim 1 wherein a flexible membrane is provided within said housing for defining said reservoir.

4. A urine collection device according to claim 1 wherein said housing is formed of a soft absorbent material such as gauze.

5. A urine collection device according to claim 1 wherein said two-way valve means comprises a section of flexible tubing which seals itself as a result of capillary attraction when selectively prohibiting the back flow of urine.

6. A urine collection device according to claim 5 wherein said receiving chamber outlet comprises a duct having an outer peripheral surface wherein said section of flexible tubing is sealingly secured to said peripheral surface of said duct.

7. A process for collecting urine from a female wherein said urine collected is suitable for laboratory examination comprising:
   providing a housing;
   positioning a receiving chamber within said housing, said receiving chamber being provided with an inlet for sealing around the urethral orifice of a female and an outlet;
   positioning a reservoir within said housing downstream of said receiving chamber outlet for receiving urine therefrom;
   providing two-way urine flow control means downstream of said receiving chamber outlet and upstream of said reservoir for passing urine from said receiving chamber through said receiving chamber outlet to said reservoir while selectively prohibiting back flow of urine from said reservoir; and
   deforming said reservoir wherein urine in said reservoir is passed back through said two-way urine flow control means to said receiving chamber wherein a urine specimen for a laboratory examination is obtained.

8. A process according to claim 7 including the step of providing a flexible tubing as said two-way urine flow control means wherein said flexible tubing passes back through said outlet for passing urine from said reservoir when said reservoir is deformed.

* * * * *